United States Patent
Hecker

(10) Patent No.: US 9,610,020 B1
(45) Date of Patent: Apr. 4, 2017

(54) APPARATUS AND METHOD FOR AUTOMATICALLY IDENTIFYING A PROBLEM WITH SENSING HEART ACTIVITY

(75) Inventor: Daniel S. Hecker, Baltimore, MD (US)

(73) Assignee: Pacesetter, Inc., Sunnyvale, CA (US)

( * ) Notice: Subject to any disclaimer, the term of this patent is extended or adjusted under 35 U.S.C. 154(b) by 1582 days.

(21) Appl. No.: 12/017,231

(22) Filed: Jan. 21, 2008

(51) Int. Cl.
*A61B 5/02* (2006.01)
*A61B 5/0245* (2006.01)
*A61B 5/024* (2006.01)
*A61N 1/36* (2006.01)

(52) U.S. Cl.
CPC ........ *A61B 5/0245* (2013.01); *A61B 5/02405* (2013.01); *A61N 1/36064* (2013.01)

(58) Field of Classification Search
CPC .............. A61N 1/37247; A61N 1/3712; A61N 1/36064; A61B 5/0245; A61B 5/02405

USPC ..................................................... 607/27–29
See application file for complete search history.

(56) References Cited

U.S. PATENT DOCUMENTS

| | | | | |
|---|---|---|---|---|
| 5,374,282 | A * | 12/1994 | Nichols et al. | ................. 607/18 |
| 5,891,178 | A | 4/1999 | Mann et al. | |
| 6,351,675 | B1 | 2/2002 | Tholen et al. | |
| 6,643,549 | B1 | 11/2003 | Bradley et al. | |
| 7,289,851 | B2 * | 10/2007 | Gunderson | .......... A61N 1/3706 |
| | | | | 607/27 |
| 2004/0015197 | A1 * | 1/2004 | Gunderson | ..................... 607/27 |

* cited by examiner

*Primary Examiner* — Michael D Abreu
(74) *Attorney, Agent, or Firm* — Theresa A. Raymer

(57) ABSTRACT

Systems and associated methods are provided for automatically identifying a problem with sensing heart activity. In use, a plurality of heartbeats is sensed utilizing an implantable medical device. Further, data associated with the heartbeats is collected and stored. To this end, a problem with the sensing of the heartbeats (e.g., oversensing, undersensing, etc.) may be automatically identified and corrected, utilizing the data.

7 Claims, 7 Drawing Sheets

APPARATUS AND METHOD FOR AUTOMATICALLY IDENTIFYING A PROBLEM WITH SENSING HEART ACTIVITY

TECHNICAL FIELD

Embodiments of the present disclosure pertain generally to implantable and external medical devices, and more particularly to methods and systems that automatically and semi-automatically recognize and correct sensing problems associated with a medical device.

BACKGROUND

An implantable medical device (IMDs) is implanted in a patient to monitor, among other things, electrical activity of a heart and to deliver appropriate electrical and/or drug therapy, as required. A wide range of implantable medical devices are available, including pacemakers, cardioverters, defibrillators, and implantable cardioverter-defibrillators. In use, IMDs may be surgically implanted in a patient to monitor the patient's cardiac activity and to provide electrical stimulation in order to correct irregular cardiac rhythms (e.g., arrhythmias).

It is important that IMDs are operated under optimal automatic sensing control parameters to provide adequate sensing, while preventing oversensing or undersensing issues in either the atrial or ventricular channels. Such oversensing refers to a state when the IMD may consider a sensed signal to be a heartbeat when, in fact, it is not one. Conversely, undersensing refers to a state when the IMD may not consider a sensed signal to be a heartbeat when, in fact, it is one. In conventional systems, such sensing problems have lead to inappropriate mode switches, rate branch discrimination, or delivery or inhibition of device therapies such as anti-tachycardia pacing, cardioversion, defibrillation shocks, etc. There is a need for a method and system that automatically recognizing and correcting sensing problems associated with an IMD. The present disclosure addresses this need and provides related advantages.

Overview

Systems and associated methods are provided for automatically identifying a problem with sensing heart activity. In use, a plurality of heartbeats is sensed utilizing an implantable medical device. Further, data associated with the heartbeats is collected and stored. To this end, a problem with the sensing of the heartbeats (e.g., oversensing, undersensing, etc.) may be automatically identified and corrected, utilizing the data.

DESCRIPTION OF EXAMPLE EMBODIMENTS

Figure 1:
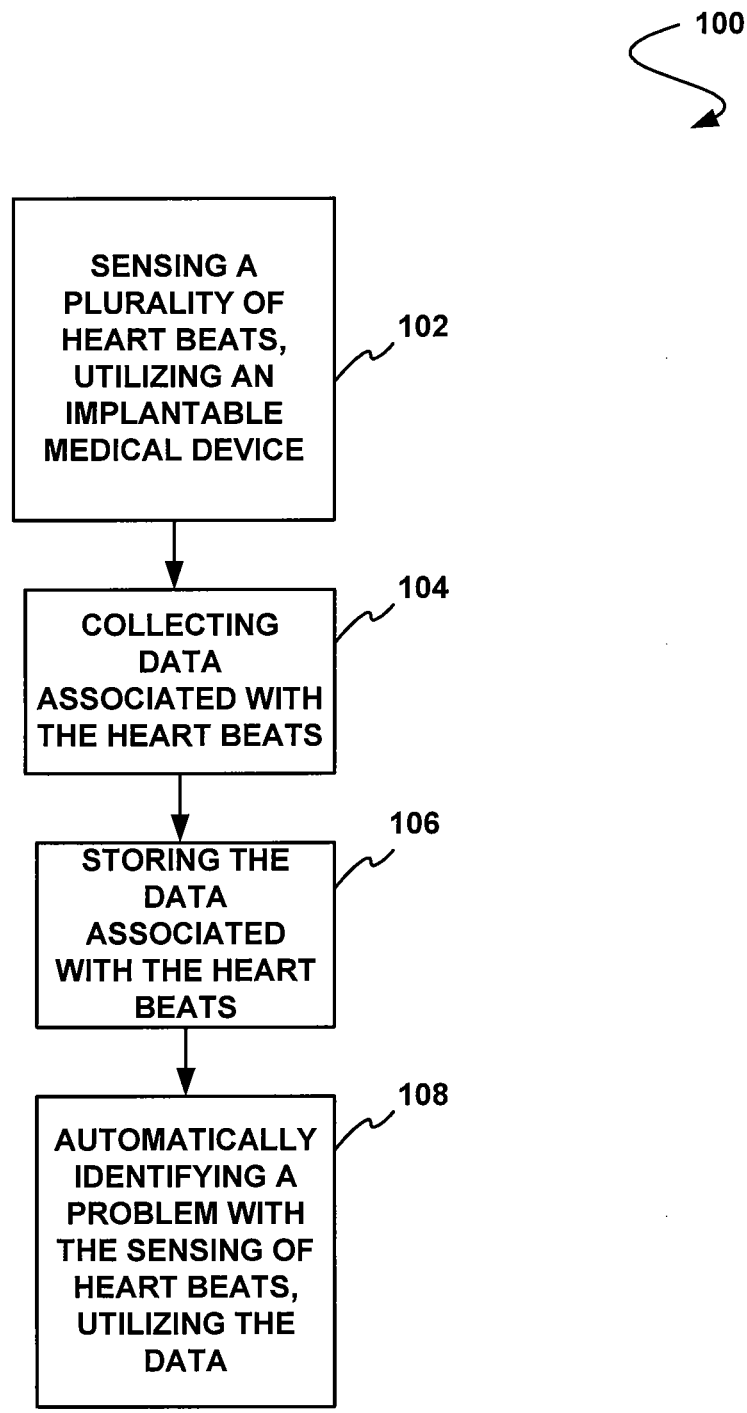
FIG. 1 illustrates a method for automatically identifying heartbeat sensing problems, in accordance with one embodiment.

FIG. 1 illustrates a method 100 for automatically identifying heartbeat sensing problems, in accordance with one embodiment. As shown, a plurality of heartbeats is sensed utilizing an implantable medical device (IMD). See operation 102. In one embodiment, the IMD may be equipped with sensors for such purpose.

In varying embodiments, the IMD may include a cardiac pacemaker, an implantable cardioverter defibrillator (ICD), an implantable drug pump, a device for sensing portions of the heart, etc. To this end, in the context of the present description, the IMD refers to any device capable of being implanted in a human patient or animal for heart-related medical purposes. More information regarding various examples of IMDs and configurations thereof will be set forth hereinafter in greater detail during the description of subsequent figures.

With continuing reference to FIG. 1, data associated with the heartbeats is collected and stored, as indicated in operations 104-106. Such data collection may be accomplished in a variety of ways. Just by way of example, a plurality of morphological pulses may be received in response to the sensing of operation 102. To this end, data in the form of a portion of the pulses, parameters associated with the pulse, and/or even the pulses themselves may be collected and stored for reasons that will soon become apparent.

In one embodiment, such data may be collected and/or stored utilizing the aforementioned IMD. To accomplish this, the IMD may be equipped with at least one circuit which may, for example, include a low-power microprocessor accompanied by memory. In other embodiments, the circuit may include a microcontroller, an embedded system, a programmable logic device such as a field-programmable logic array, a combinatorial implementation of a state machine, and/or any other type of circuitry, for that matter.

In still additional embodiments, the collection and/or storage may be carried out in any context, with or without the IMD. For example, the operations 104-106 may, in one embodiment, involve the use of a circuit associated with an external device. In one possible embodiment, the data may even be collected over a network. Of course, it is contemplated that any one or more aspects of the method 100 may or may not be carried out utilizing software in conjunction with the aforementioned circuit(s).

In various embodiments, the data collected and/or stored in operations 104-106 may be associated with each of a plurality of heart chambers. For example, the data may be gathered from a left atrial sensor, a right atrial sensor, a right ventricular sensor, and/or a left ventricular sensor. In yet another optional embodiment, at least a portion of the data may be associated with a combination of the aforementioned sensors. For example, the data may be collected based on input from a left atrial sensor and a right atrial sensor, a right ventricular sensor and a left ventricular sensor, a left atrial sensor and a left ventricular sensor, and/or any other combination, for that matter.

To this end, a problem with the sensing of heartbeats may be automatically identified, utilizing the data. See operation 108. For example, in one possible embodiment, a baseline of heart activity may be determined utilizing the data. Such baseline may be predetermined, user-configured to cover a certain timeframe, etc. Thus the baseline may be compared to current heart activity, such that a problem may be automatically identified based on the comparison. For example, if it is found that non-physiological activity is identified (which did not exist with respect to the baseline), such may be an indication that a sensing problem exists. By this design, an IMD may be able to self-recognize a heartbeat sensing problem.

While not shown in FIG. 1, any problem that is identified in operation 108 may optionally be corrected. Such correction may be manual and/or automatic. To accomplish this, a plurality of parameters associated with the IMD may be adjusted. Examples of such parameters may include, but are certainly not limited to, a threshold start value, a decay delay value, a sense refractory value, a pace refractory value, a far-R/PVAB suppression value, and a maximum sensitivity value. The foregoing adjustment technique may, in one embodiment, be continuous as well as incorporate feedback, tuning, as desired. Additional information regarding various ways that problems may be addressed will be set forth hereinafter in greater detail.

More illustrative information will now be set forth regarding various optional architectures and features of different embodiments with which the foregoing technique may or may not be implemented, per the desires of the user. It should be strongly noted that the following information is set forth for illustrative purposes and should not be construed as limiting in any manner. Any of the following features may be optionally incorporated with or without the other features described.

Figure 2:
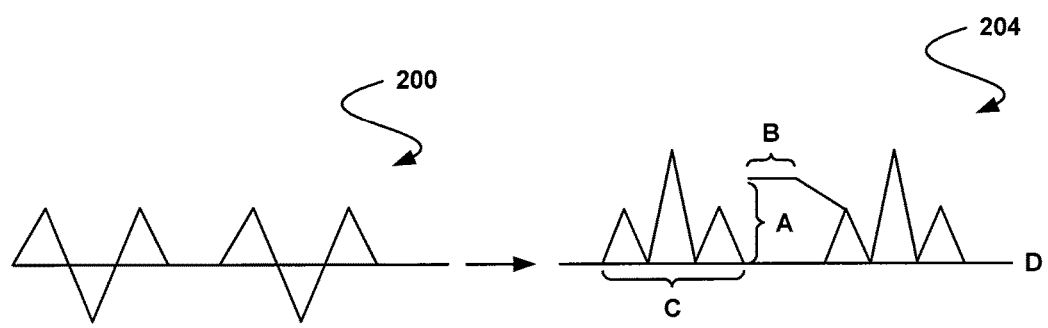
FIG. 2 illustrates a plurality of morphological pulses and associated control parameters, in accordance with another embodiment.

FIG. 2 illustrates a plurality of morphological pulses 200 and associated control parameters 204, in accordance with one embodiment. As an option, the morphological pulses 200 and associated data may be collected and stored in the context of the operations 104-106 of the method 100 of FIG. 1. In use, the parameters 204 may be adjusted for addressing a problem (e.g., oversensing/undersensing, etc.) with heartbeat sensing. It should be noted that the definitions provided above may equally apply to the present description.

In the context of the present description, such morphological pulses 200 may include any changes in association with a morphological signal that may be used to monitor a heart of a human or animal patient. For example, in one exemplary embodiment, the morphological pulses may include peaks representative of pulses that are defined by a point of maximum amplitude and two continuously downward-sloping sides, as shown.

Still yet, in various embodiments, such morphological pulses may be associated with at least one QRS complex. A sequence of QRS complexes produced by a beating heart creates an electrogram (EGM). In one embodiment, the EGM may be a custom EGM, where at least a portion of collected data may be associated with a selected combination of a plurality of right/left/atrial/ventricular sensors, etc. In use, such EGM signals, etc. may be monitored to collect data in the form of EGM characteristics such as amplitude, polarity, shape, etc. associated with related pulses which might be helpful in monitoring a patient's cardiac activity.

With continuing reference to FIG. 2, the parameters 204 (e.g., A-D) are shown in association with a rectified version of the morphological pulses 200. In use, such parameters 204 may be adjusted for addressing a problem (e.g., over-sensing/undersensing, etc.) with heartbeat sensing. As mentioned earlier, such problem may be automatically identified based on data collected in association with heart activity.

As shown, a threshold start value A refers to a percentage of a maximum QRS complex magnitude of the rectified incoming signal that is required before the IMD will recognize it as a QRS complex. Exemplary threshold start values include, but are not limited to 50, 62.5, 75, and 100%.

Further, a decay delay B refers to an amount of time that sensitivity remains at the threshold start value A before such sensitivity increases in the manner shown. Thus, the larger the decay delay B, the less likely a subsequent signal will be recognized during a time period that directly follows a QRS complex (which could be noise, etc.). Exemplary decay delay values include, but are not limited to 0, 30, 60, 95, 125, 160, 190, and 220 milliseconds.

Even still, a sense refractory value C refers to a maximum acceptable duration of a QRS complex. In healthy patients who typically have a shorter QRS complex duration, a lower sense refractory value C may be chosen to reduce the chances of two QRS complexes being counted as one. However, a greater sense refractory value C may be chosen for less-than healthy patients with elongated QRS complexes (e.g., due to heart contraction disychronicity, etc.). Exemplary sense refractory values include, but are not limited to a range of 93, 125, and 157 milliseconds, for instance.

A pace refractory value (not shown) refers to a blanking period that follows a shock administered to the heart, for the purpose of sensing a paced pulse, but avoiding the unwanted detection of a contraction that may result from the paced pulse. Exemplary pace refractory values include, but are not limited to 125, 160, 190, 220, 250, 280, 310, 340, 370, 400, 440, and 470 milliseconds, for instance.

A far-R/PVAB suppression value (also not shown) refers to a blanking period that prevents an atrial sensor from detecting a contraction of a ventricle. For example, the far-R/PVAB suppression value may include a period of time after a ventricle contraction, during which any input from an atrial sensor is ignored. Exemplary far-R/PVAB suppression values include, but are not limited to a range of 20 to 250 milliseconds (in 10 millisecond increments), for instance.

Finally, a maximum sensitivity value D may refer to a smallest magnitude of a QRS complex pulse that is capable of being sensed.

Figure 3:
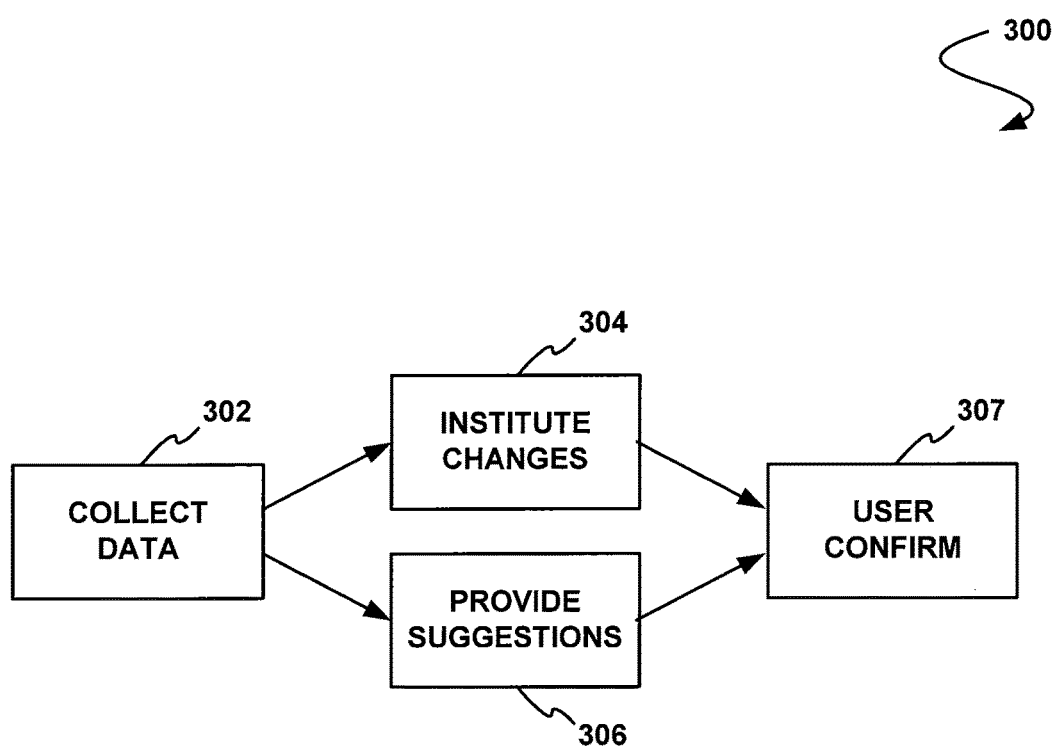
FIG. 3 illustrates a system for automatically identifying heartbeat sensing problems and correcting the same, in accordance with another embodiment.

FIG. 3 illustrates a system 300 for automatically identifying heartbeat sensing problems and correcting the same, in accordance with another embodiment. As an option, the system 300 may incorporate the functionality set forth in the previous figures. Of course, however, it should be noted that the system 300 may be implemented in any desired environment. Further, the definitions provided above may equally apply to the present description.

As shown, data associated with sensed heart activity is collected in operation 302. As mentioned earlier, such data may describe any heart chamber or combination thereof. For example, such data may refer to a signal duration, amplitude, peaks, and/or any other aspect of the heart activity. Further, such data may be stored in conjunction with an IMD and/or be transmitted to an external device for external storage. Still yet, such external device may be local to the IMD, coupled via a network such as the Internet or a telecommunication network, etc.

In different embodiments, data collection may be intermittent, based on a triggered event such as abnormal heart activity, a predetermined schedule, a random schedule, etc. Other embodiments may be provided for continuous, ongoing data collection as well. For example, in some embodiments, such data collection may be continuous over a period of 1 minute, 1 hour, 1 day, 1 month, etc. Of course, such data collection may span a minimal duration or any period that is supported by memory constraints.

With such data collected, any identified problem may be addressed by automatically and/or manually instituting changes as noted in operation 304. Such changes may, for example, involve adjusting one of a plurality of sensing parameters optimal threshold start, decay delay, sense refractory value, pace refractory value, far-R/PVAB suppression, and maximum sensitivity values. Note the parameters 204 of FIG. 2, for example. Instead of, or in combination with, the instituted changes, various suggestions may be made. See operation 306. In any case, operations 304 and/or 306 may be carried out by a doctor, an IMD programmer, a technician, an automated mechanism, etc.

In the end, a user may or may not choose to confirm any changes or suggestions. See operation 307. Such confirmation may be made on a manual and/or automated basis (via a graphical user interface, etc.).

Figure 4A:
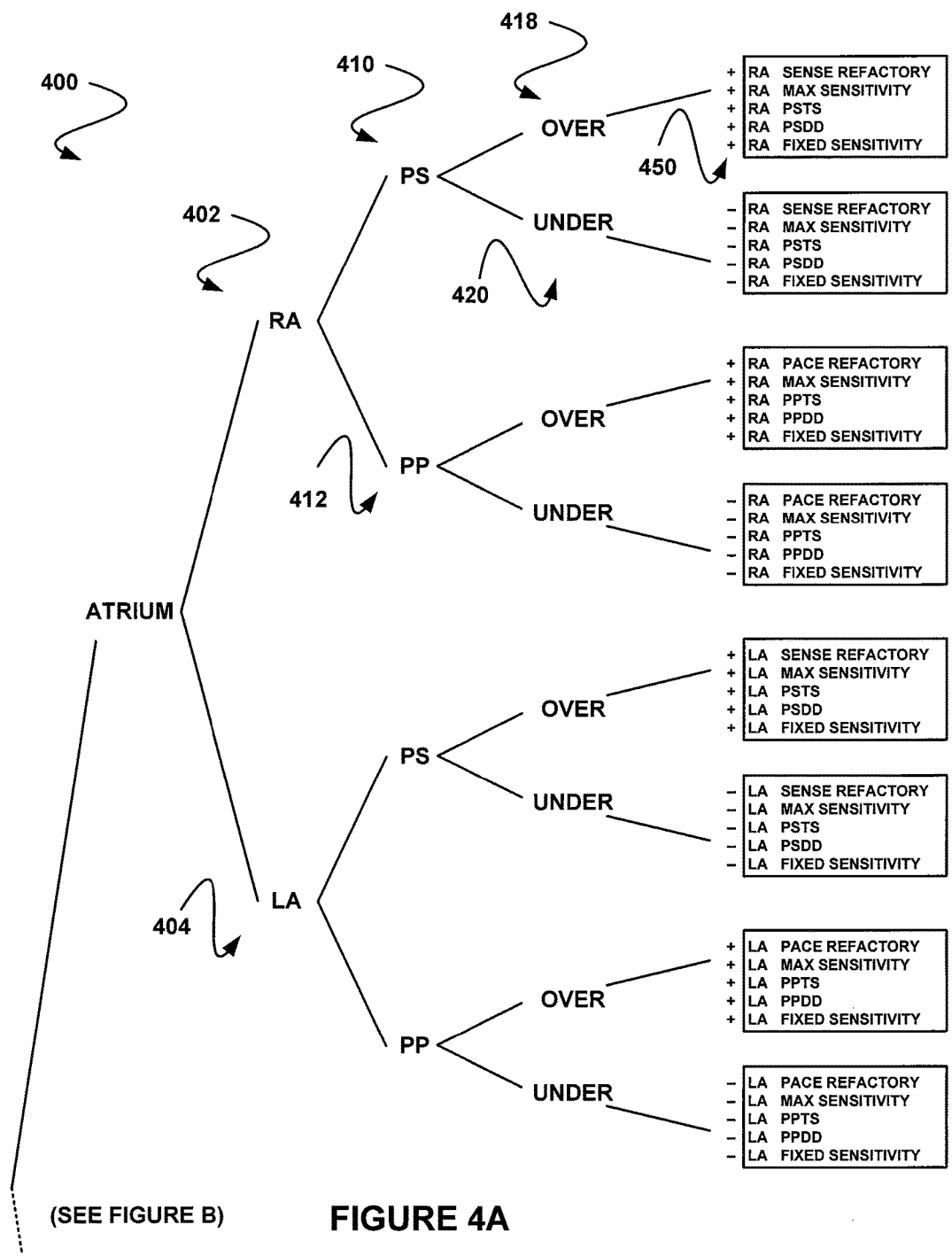
FIGS. 4A-4B illustrate a decision tree for determining a possible solution to an oversensing or undersensing problem, in accordance with another embodiment.
Figure 4B:
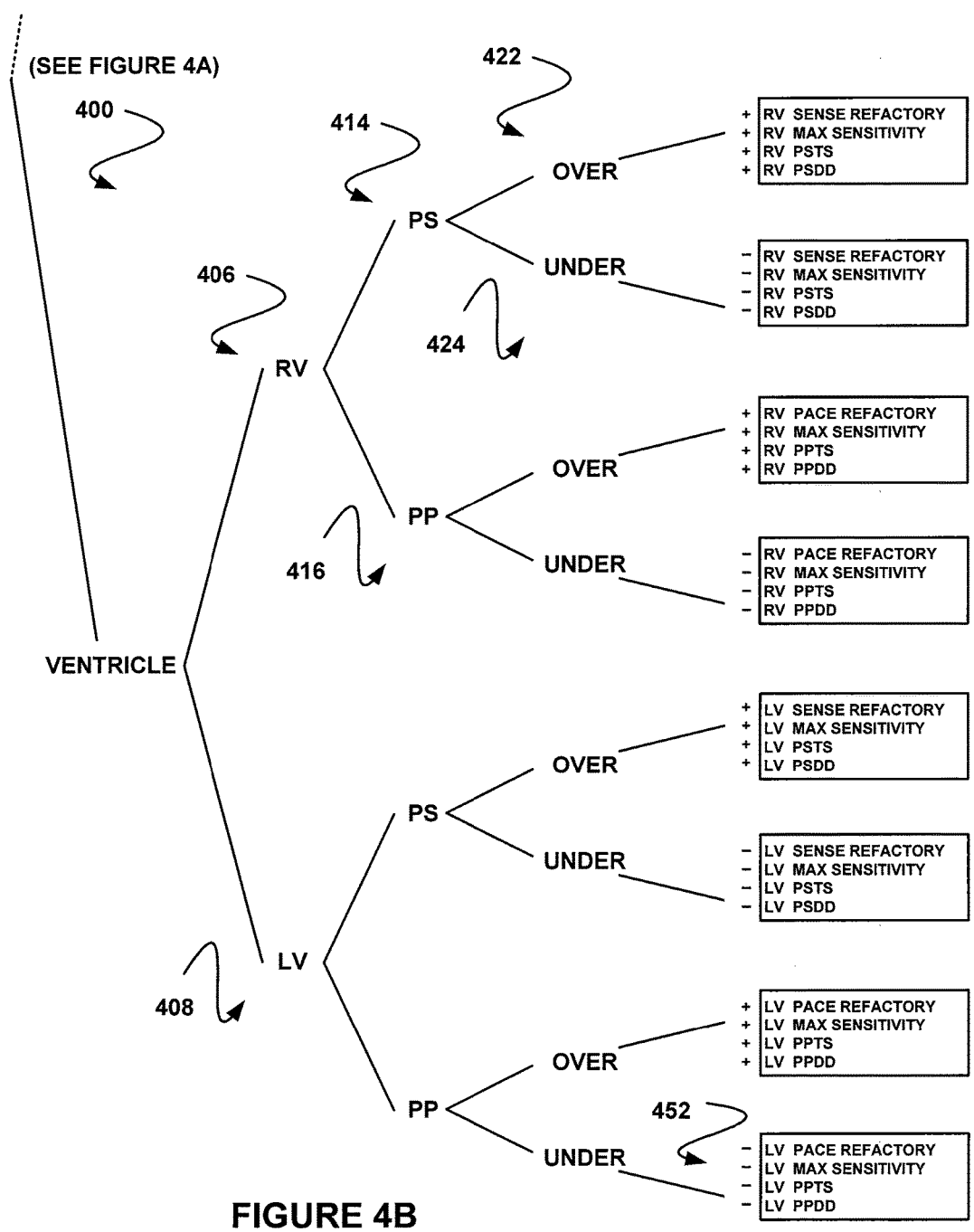

FIGS. 4A-4B illustrate a decision tree 400 for determining a possible solution to an oversensing or undersensing problem, in accordance with one embodiment. As an option, the decision tree 400 may be used in conjunction with the architecture and/or functionality set forth in the previous figures. For example, such decision tree 400 may be used in the context of operations 304-306 of FIG. 3. Of course, however, it should be noted that the decision tree 400 may be used in any desired environment. Yet again, the definitions provided above may equally apply to the present description.

As mentioned earlier, when attempting to identify a heartbeat sensing problem, data may be gathered from a left atrial sensor, a right atrial sensor, a right ventricular sensor, and/or a left ventricular sensor. Depending on where a problem has been identified, various branches of the decision tree 400 may be traversed. For example, if a problem is right or left atrium-specific, branches 402 and 404 of FIG. 4A would be traversed, respectively. On the other hand, if a problem is right or left ventricle-specific, branches 406 and 408 of FIG. 4B would be traversed, respectively.

Continuing on, it may also be determined whether the problem is post-sensed (PS) or post-paced (PP). In other words, in the context of a post-sensed (PS) problem, a problem may arise after a naturally occurring heartbeat is sensed. On the other hand, in the context of a post-paced (PP) problem, a problem may arise after sensing a heartbeat that occurred in response to an administered therapy.

If a problem is post-sensed (PS) or post-paced (PP)-specific in association with an atrial chamber, branches 410 and 412 of FIG. 4A (in the case of a right atrium) would be traversed, respectively. On the other hand, if a problem is post-sensed (PS) or post-paced (PP)-specific in association with a ventricular chamber, branches 414 and 416 of FIG. 4B (in the case of a right ventricle) would be traversed, respectively.

Still yet, it may be determined whether the problem is with oversensing or undersensing. As mentioned earlier, such oversensing refers to a state when the IMD may consider a sensed signal to be a heartbeat when, in fact, it is not one. Conversely, undersensing refers to a state when the IMD may not consider a sensed signal to be a heartbeat when, in fact, it is one.

If a problem is oversensing or undersensing in association with an atrial chamber, branches 418 and 420 of FIG. 4A (in the case of a right atrium that is experiencing a post-sensed problem) would be traversed, respectively. On the other hand, if a problem is oversensing or undersensing in association with a ventricle chamber, branches 422 and 424 of FIG. 4B (in the case of a right ventricle that is experiencing a post-sensed problem) would be traversed, respectively.

By following the decision tree 400 in such a manner, it may be determined which of a plurality of parameters (see FIG. 2) are appropriate for adjustment and further whether a positive (+) or negative (−) adjustment is appropriate. To this end, appropriate parameters may be adjusted (in the appropriate direction) based on a heart chamber corresponding with a sensor associated with the problem, based on whether the problem includes an oversensing problem or an undersensing problem, etc.

In the case indicated by numeral 450 in FIG. 4A, any one or more of the following values may be augmented (+) in association with the right atrium (RA): sense refractory value, maximum sensitivity value, post-sensed threshold start (PSTS) value, post-sensed decay delay (PSDD) value, and fixed sensitivity value. In the case indicated by numeral 452 in FIG. 4B, as an additional example, any one or more of the following values may be decreased (−) in association with the left ventricle (LV): pace refractory value, maximum sensitivity value, post-paced threshold start (PPTS) value, and post-paced decay delay (PPDD) value.

An example will now be set forth regarding one way in which such appropriate parameters may be adjusted. If, during data collection, it is determined that post-sensed oversensing is occurring, a worst case scenario or small sample subset of oversensing may first be identified. This may be represented by a smallest intrinsic signal, largest oversensed signal, and longest intrinsic signal to oversensed interval. When the worst case example has been identified, the IMD or external device may measure a maximum baseline-to-peak amplitude in a sense refractory of the rectified intrinsic signal. Next, the same measurement may be repeated on the oversensed signal.

Then, an interval between the two sensed events may be calculated. Finally, any combination of the following parameters may be made such that the programmed maximum sensitivity may be reached in the shortest period of time, while preventing oversensing: maximum sensitivity, threshold start, decay delay, far-R/PVAB suppression, and sense refractory.

On the other hand, if the IMD is oversensing post-paced, a worst case scenario or small sample subset of oversensing may be identified. This may be represented by a largest oversensed signal and a longest pace pulse to oversensed signal interval. Once such a worst case example has been established, a maximum baseline-to-peak amplitude in a sense refractory of the rectified oversensed signal may be identified.

Finally, an interval between the paced and oversensed events may be calculated. Further, it may be determined whether to decrease the maximum sensitivity or increase the threshold start, decay delay, far-R/PVAB suppression, and/or pace refractory values.

Figure 5:
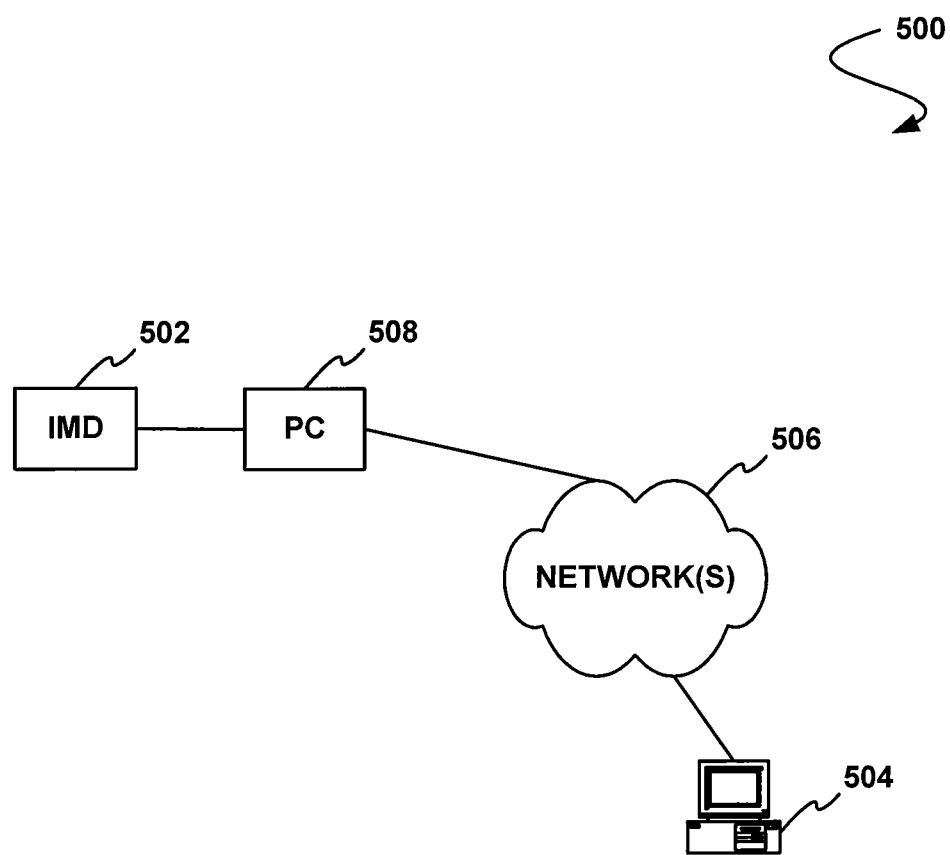
FIG. 5 illustrates a system for automatically identifying heartbeat sensing problems, in accordance with one embodiment.

FIG. 5 illustrates a system 500 for automatically identifying heartbeat sensing problems, in accordance with one embodiment. As an option, the system 500 may incorporate the functionality set forth in the previous figures. Of course, however, it should be noted that the system 500 may be implemented in any desired environment. Again, the definitions provided above may equally apply to the present description.

As shown, included is an IMD 502 which remains in communication with an external device 504 via at least one network 506. The external device 504 may include a computer equipped with one or more of the following components: a processor, memory, software, a display, various input/output devices, etc. Further, such computer may take the form of a desktop computer, lap-top computer, hand-held computer, mobile phone, personal digital assistant (PDA), peripheral (e.g., printer, etc.), any component of a computer, etc. The display may be a touch-sensitive display and may comprise a sensing screen. Thus the external device 504 refers to any type of device that is external to the patient.

Still yet, the one or more networks 506 may each take any form including, but not limited to a local area network (LAN), a wireless network, a wide area network (WAN) such as the Internet, peer-to-peer network, etc. Of course, if more than one network 506 is provided, such networks 506 may include similar or dissimilar network types. In use, the one or more networks 506 provide for communication between the IMD 502 and the external device 504.

In one embodiment, a computer 508 may be employed to provide an interface between the IMD 502 and the network 506. As an option, such computer 508 may include a digital telemetry module (DTM) or the like. In such embodiment, the user may connect electrodes from the patient's wrists, finger tips, chest, etc. to the computer 508 so that IMD-related data (e.g., EGM signals, any other data capable of being collected by the IMD, etc.) may be transmitted from the IMD 502 to the network 506, etc. Of course, however, the computer 508 may include any computer, as defined above with respect to the external device 504, capable of providing an interface between the IMD 502 and the network 506.

In the present embodiment, data may be collected from (and even stored at) the IMD 502 for transmission over the network 506 (via the computer 508), for the purpose of being stored on the external device 504. By this design, the external device 506 may be used to automatically identify sensing problems at the IMD 502. Still yet, the external device 504 may even be used to correct such problems. As mentioned earlier, the present embodiment is set forth for illustrative purposes only and should not be construed as limiting in any manner. For example, embodiments are contemplated without the use of the network 506, computer 508, and/or external device 504.

Figure 6:
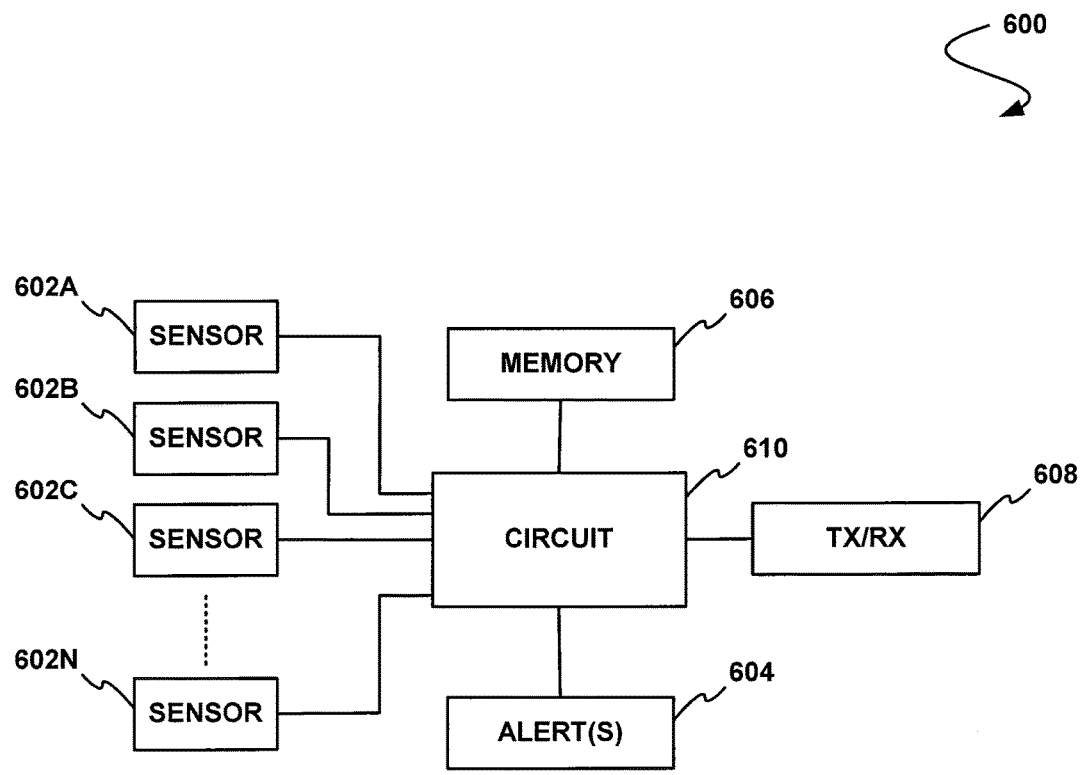
FIG. 6 illustrates an implantable medical device (IMD), in accordance with one embodiment.

FIG. 6 illustrates an IMD 600, in accordance with one embodiment. As an option, the IMD 600 may incorporate the functionality set forth in the previous figures. In one embodiment, the IMD 600 may include the IMD 502 of FIG. 5. Of course, however, it should be noted that the IMD 600 may be implemented in any desired environment. Again, the definitions provided above may equally apply to the present description.

As shown, the IMD 600 includes a circuit 610 in communication with a plurality of peripheral components. As mentioned earlier, the circuit 610 may include a low-power microprocessor, a microcontroller, an embedded system, a programmable logic device such as a field-programmable logic array, a combinatorial implementation of a state machine, and/or any other type of circuitry.

In one embodiment, the circuit 610 will determine optimal sensing parameters, including one or more of a threshold start, decay delay, sense refractory, pace refractory, far-R/PVAB suppression, and/or maximum sensitivity values. Once the calculation is run, the circuit 610 may display to a user through a graphical interface (such as on the display of external device 504) the current non-ideal programmed settings and the suggested ideal settings while graphically depicting both parameter sets as an overlay on either the stored or frozen real-time electrogram where a sensing anomaly has occurred. A user can then make the necessary adjustments and monitor the patient at the improved setting.

The aforementioned peripheral components are shown to include a plurality of sensors 602A, 602B, 602C, and 602N (hereinafter "602A-N"), memory 606, a transceiver 608, and one or more alerts 604. While the various peripheral components are shown in FIG. 6 to be discrete components, it should be understood that one or more of such components may be integrated in a single unillustrated IMD housing.

In one embodiment, the transceiver 608 may include an integrated radio frequency telemetry unit. Other embodiments of the transceiver 608 are possible, including acoustic, optic, electrostatic, and magnetic-type transceivers. In yet another embodiment, a receiver component of the transceiver 608 may simply take the form of a reed switch capable of sensing the presence of a strong magnet, so that the IMD can be turned on and off externally, but lacks post-manufacturing programmability. In still other embodiments, the transceiver 608 might not be included, so that the IMD lacks the ability to receive or transmit information.

The alert 604 may include a vibratory or audible alert capable of vibrating or creating an audible signal when activated. In use, the alert 604 may serve any desired purpose including, but not limited to alerting the user when conditions require a response, such as contacting a physician, seeking immediate emergency medical attention, adjusting pharmacologic regimens, ceasing exercise or other activities, seeking technical assistance to remedy any deficiency in the performance or integrity of the IMD 600, etc.

For example, the alert 604 may be triggered in response to a detection of issues directly related to the performance or integrity of the IMD 600 (e.g., lead fractures, insulation problems, battery depletion, software malfunctions, etc. that may lead to sensing problems). In addition, the alert 604 may be triggered in response to clinical conditions that can be detected by the IMD 600 (e.g., a presence of an otherwise imperceptible rhythm disorder, potentially significant levels of ischemia, even non-cardiac conditions unrelated to the primary purpose of the IMD such as glycemic levels, etc.).

The foregoing description has set forth only a few of the many possible implementations. For this reason, this detailed description is intended by way of illustration, and not by way of limitations. Variations and modifications of the embodiments disclosed herein may be made based on the description set forth herein, without departing from the scope and spirit of the present application.

It is only the following claims, including all equivalents, that are intended to define the scope of the various embodiments. Moreover, the embodiments described above are specifically contemplated to be used alone as well as in various combinations. Accordingly, other embodiments, variations, and improvements not described herein are not necessarily excluded.

What is claimed is:

1. A method for optimizing sensing control parameters associated with an implantable medical device (IMD), the method comprising:

sensing a plurality of baseline heartbeats, utilizing the IMD;

collecting data associated with the plurality of sensed baseline heartbeats;

storing the data associated with the plurality of sensed baseline heartbeats in a memory;

programming first settings of sensing control parameters of the IMD;

sensing a plurality of non-baseline heartbeats using the IMD programmed to use the first settings of the sensing control parameters;

collecting data associated with the plurality of sensed non-baseline heartbeats;
using a circuit to automatically identify a problem with the sensing of the heartbeats using the first settings of sensing control parameters by comparing the data associated with the plurality of sensed baseline heartbeats to the data associated with the plurality of sensed non-baseline heartbeats;
automatically determining which chamber of the heart is associated with the problem;
automatically determining whether the plurality of sensed non-baseline heartbeats are post-sensed or post-paced, wherein a post-sensed heartbeat is a naturally occurring heartbeat and wherein a post-paced heartbeat is a heartbeat that occurred in response to an administered therapy;
automatically determining whether the problem with sensing is over or under sensing; and
when the problem with sensing is post-sensed oversensing, automatically determining from the data associated with the plurality of sensed non-baseline heartbeats a worst case scenario by determining:
a smallest intrinsic signal,
a largest oversensed signal, and
a longest time interval between an intrinsic signal and an oversensed signal;
measuring a maximum baseline-to-peak amplitude in a sense refractory of the rectified smallest intrinsic signal of the worst case scenario;
measuring a maximum baseline-to-peak amplitude in a sense refractory of the rectified largest oversensed signal of the worst case scenario; and
at least one of:
adjusting the settings of sensing control parameters of the IMD based on the worst case scenario by programming the IMD to use a second set of sensing control parameters, using the adjusted settings to determine treatment to be delivered, and delivering the determined treatment; or
using the microprocessor of the IMD to display data comprising the current setting of the sensing control parameters of the IMD and a suggested setting of the sensing control parameters of the IMD.

2. The method of claim 1, wherein at least a portion of the data is associated with a combination of sensors selected from the group consisting of a left atrial sensor, a right atrial sensor, a left ventricular sensor, and a right ventricular sensor.

3. The method of claim 1 further comprising automatically correcting the problem using the microprocessor of the IMD.

4. The method of claim 1, wherein the parameters include at least one of a threshold start value, a decay delay value, a sense refractory value, a pace refractory value, a far-R/PVAB suppression value, or a maximum sensitivity value.

5. The method of claim 1 further comprising displaying, using the microprocessor of the IMD, graphic overlays that depict an automatic sensing control decay curve for the current setting of the IMD and the suggested setting.

6. The method of claim 1, wherein using a microprocessor of the IMD to sound an alarm comprises generating a vibratory or audible signal using an alert of the IMD in response to a problem with programmed sensing parameters identified.

7. A method for optimizing sensing control parameters associated with an implantable medical device (IMD), the method comprising:
sensing a plurality of baseline heartbeats, utilizing the IMD;
collecting data associated with the plurality of sensed baseline heartbeats;
storing the data associated with the plurality of sensed baseline heartbeats;
programming settings of sensing control parameters of the IMD;
sensing a plurality of non-baseline heartbeats using the programmed settings of the sensing control parameters of the IMD;
collecting data associated with the first plurality of sensed non-baseline heartbeats;
automatically identifying an problem with the sensing of the heartbeats using the programmed setting of sensing control parameters by comparing the data associated with the plurality of sensed baseline heartbeats to the data associated with the plurality of sensed non-baseline heartbeats;
automatically determining which chamber of the heart is associated with the problem;
automatically determining whether each of the first plurality of sensed non-baseline heartbeats is an intrinsic signal or an oversensed signal by comparing the data associated with the plurality of sensed baseline heartbeats to the data associated with the plurality of sensed non-baseline heartbeats;
automatically determining whether the problem is a post-sensed problem or a post-paced problem, wherein a post-sensed problem is a problem arising after a naturally occurring heartbeat is sensed and wherein a post-paced problem is a problem arising after sensing a heartbeat that occurred in response to an administered therapy; and
when the problem is post-sensed oversensing, automatically, using a microprocessor:
determining from the data associated with the plurality of sensed non-baseline heartbeats a worst case scenario by determining:
a smallest intrinsic signal,
a largest oversensed signal, and
a longest time interval between an intrinsic signal and an oversensed signal;
measuring a maximum baseline-to-peak amplitude in a sense refractory of the rectified smallest intrinsic signal of the worst case scenario;
measuring a maximum baseline-to-peak amplitude in a sense refractory of the rectified largest oversensed signal of the worst case scenario; and
using the worst case scenario, at least one of:
adjusting the settings of sensing control parameters of the IMD by programming the IMD to use a second set of sensing control parameters, using the second set of sensing control parameters to determine treatment to be delivered, and delivering the determined treatment; or
using the microprocessor of the IMD to determine a suggested setting of the sensing control parameters of the IMD and display data comprising at least one of:
suggested settings of sensing control parameters, or
graphic overlays that depict an automatic sensing control decay curve for the current setting of the IMD and the suggested setting.

* * * * *